United States Patent [19]

Friese

[11] Patent Number: 4,498,218
[45] Date of Patent: Feb. 12, 1985

[54] APPARATUS FOR TRANSMITTING A TAMPON BLANK TO A TAMPON PRESS

[75] Inventor: Axel Friese, Wuppertal, Fed. Rep. of Germany

[73] Assignee: Dr. Carl Hahn G.m.b.H., Dusseldorf, Fed. Rep. of Germany

[21] Appl. No.: 413,369

[22] PCT Filed: Dec. 21, 1981

[86] PCT No.: PCT/DE81/00232
§ 371 Date: Aug. 13, 1982
§ 102(e) Date: Aug. 13, 1982

[87] PCT Pub. No.: WO82/02336
PCT Pub. Date: Jul. 22, 1982

[30] Foreign Application Priority Data

Dec. 31, 1980 [DE] Fed. Rep. of Germany ....... 3049581

[51] Int. Cl.³ .............................................. A61F 13/20
[52] U.S. Cl. ..................................................... 28/119
[58] Field of Search ........................... 28/118, 119, 120

[56] References Cited

U.S. PATENT DOCUMENTS 2,152,230  3/1939  Webb ..................................... 28/120
3,946,463  3/1976  Warncke et al. ..................... 28/120
4,453,296  6/1984  Friese ................................... 28/119

Primary Examiner—Robert R. Mackey
Attorney, Agent, or Firm—Jason Lipow

[57] ABSTRACT

An apparatus for compressing a blank into a compressed tampon is provided. In the direction of its central axis, the apparatus comprises in succession a push rod, a transmitting device, a tampon press and an ejector mandrel. The carrier jaws of the transmitting device are concentrically movable with respect to the axis and have a closed passage channel whose cross-section is suitable for the blank or the pressed tampon. The cross-section of the push rod is notably smaller than the passage opening provided in the open portion of the carrier jaws for the tampon blank. The carrier jaws have in the direction of the axis, a width corresponding to at least the length of the blank. The tampon press has pressing jaws which are radially movable with respect to the axis between a receiving position of the tampon blank and a pressed position. The ejector mandrel serves to eject the tampon out of the tampon press back into the transmitting device and against the push rod.

7 Claims, 10 Drawing Figures

APPARATUS FOR TRANSMITTING A TAMPON BLANK TO A TAMPON PRESS

BACKGROUND OF THE INVENTION

The invention relates to an apparatus for transmitting a blank of absorbent material, particularly fiber material, for the manufacture of tampons, particularly for feminine hygiene, to a tampon press.

Starting material for the manufacture of such tampons is usually a cotton fleece which, after leaving a carding machine, is divided into small short webs and rolled up first to loose rolls. These rolls, which approximately have the length of the finished tampon, are subsequently radially pressed together to a smaller diameter and, if necessary, subjected to an axial compression. As required, the cotton fleece sections can be provided with a withdrawl cord before being rolled up.

An apparatus of the type mentioned above is known from German Pat. No. 21 14 530. The bearing surface associated to the transmitting device for the tampon blank consists of a shaping jaw which is movable up and down and by means of which the blank is raised to the position for transmission into the tampon press in simultaneously being pre-shaped before the blank is inserted into the tampon press by means of a mandrel and is, after having been pressed to a tampon, ejected at the other side of the press by an ejector mandrel.

From German Pat. No. 22 53 180, there is known an apparatus for fixing the free end of a withdrawal cord at a tampon wadding roll, wherein, before the rolling up of the strip of nonwoven material starts, the free end of the withdrawal cord is sucked into the position pointing away from the strip of nonwoven material and the suction effect is maintained during the winding procedure. The withdrawal cord is pulled out of its holder when the roll is transported onwards to an applying station for the withdrawal cord, where the withdrawal cord is sucked into a cylinder and then pressed onto the end face of the roll in a random position. The apparatus consists of a cylinder housing, the cylinder opening of which is disposed coaxially opposite each of the cylindrical blanks and receives a piston-type slide valve which is provided with perforations, it being possible to connect the cylinder to a source of suction air. On the side of the roll facing away from the cylinder housing, there is provided a stop face for said cylinder housing.

According to German Pat. No. 915,382, a withdrawal cord is brought into a vertical position to a cotton fleece guided through a slot of a winding mandrel and is stripped over said winding mandrel by two sliders, wherein, after the fleece has been rolled to a tampon, the projecting ends of the withdrawal cord wound around the mandrel, are pressed against the end of the blank by a stripper.

SUMMARY OF THE INVENTION

The invention, on the other hand, is based on the object to improve the apparatus for transmitting tampon blanks to a tampon press, in utilizing the smallest possible space and reducing the heights of lift of the movable machine parts, in such a manner that the tampon can also be ejected to the side from which it has been introduced into the press while being satisfactorily guided by the transmitting device and can, if necessary, additionally be subjected to an axial pressing procedure.

The invention solves this problem by making improvements in the prior apparatus. Specifically, improvements are made in an apparatus of the kind for compressing a blank comprising absorbent material into a compressed tampon wherein said blank is placed into a transmission device located upstream of a tampon press. The blank is transmitted from said transmission device into the tampon press. The blank is compressed within the tampon press into a compressed tampon and then ejected from the press. The tampon press is of the type which comprises pressing jaws, radially movable in a plane transverse to the central axis of the apparatus. The pressing jaws form a continous press opening.

The improvement comprises including as the transmission device, a stationary basic body having an axis aligned with the central axis of the apparatus. A plurality of carrier jaws are movably affixed to the basic body. The carrier jaws are movable with respect to each other so as to form, in a first position, a first passage opening having closed walls defined by the jaws for enclosing the blank. The jaws are also movable with respect to each other so as to form, in a second position, a second passage opening having closed walls defined by the jaws for enclosing the compressed tampon. The first and second passage openings are coaxial with the central axis of the apparatus and the carrier jaws have a length in the direction of the central axis of at least equal to the length of the blank.

A push rod is axially positioned upstream of the transmission device and is adapted to reciprocate into and out of the first passage opening for transmitting the blank into the press opening. An ejector mandrel is axially positioned downstream of the tampon press and has a diameter smaller than that of the compressed tampon. The ejector mandrel is adapted to reciprocate into and out of the press opening. Means are provided for moving the carrier jaws into the first position and emplacing a tampon blank into the first passage opening. Means are also provided for reciprocating the push rod to transmit the blank from the transmission device into the tampon press. Means are provided for compressing the blank in the tampon press. Means are provided for moving the carrier jaws into the second position and for reciprocating the push rod to close the upstream end of the second passage opening. Finally, means are provided for reciprocating the ejector mandrel for ejecting the compressed tampon into the second passage opening of the transmission device.

Hereby is is achieved that only a single transmitting device is required for the transfer of the blank into the press and the receipt of the tampon from the press. Due to the common movement of the carrier jaws between the first position for the receipt of the blanks and the second position for the receipt of the tampon, which movement is centered to the central axis of the apparatus, the inertia forces to be overcome are considerably reduced so that the operation of the transmitting device can without difficulty be adjusted to the cycle of the press. Reciprocating masses are reduced to a minimum, the short lifting heights of the push-rod ensuring a high production rate of the press. The closed wall of the passage opening, formed by the carrier jaws, as well as a length thereof corresponding at least to the length of the blank in the direction of the central axis of the apparatus ensures an unobjectionable guiding of the blank or tampon, respectively, regardless of the passage opening of the carrier jaws in the first and second positions, which is adapted to the cross-section of the blank or tampon, respectively. Due to the arrangement of the push-rod, which is disposed upstream of the transmitting device, and of the ejector mandrel on the side of the tampon press facing away from the transmitting device, there is finally also possible, in dependence on the stroke of the ejector mandrel, an axial pressing of the tampon which is thus effected when the tampon is ejected from the press during a working movement of the ejector mandrel.

In a specific embodiment, provided for transmitting a tampon blank having a withdrawal cord attached thereto to the tampon press, the length of the carrier jaws in the direction of the central axis is provided greater than the free length of the withdrawal cord of the tampon blank.

This presents the special advantage that the withdrawal cord, after insertion of the blank into the press by the push-rod, is held by the carrier jaws forming the passage opening and is consequently safely protected from being affected by the tampon press. Since the ejector mandrel ejects the tampon after its pressing into the passage opening of the carrier jaws in their second position provided for the tampon with correspondingly smaller cross-section and displaces it until it comes into contact with the push-rod closing the passage opening, the withdrawal cord, extending between the tampon and the push-rod in the passage opening formed by the carrier jaws, is thereby at the same time automatically substantially helically pushed together and pressed against the withdrawal end of the tampon in becoming simultaneously hooked with the fibers of the tampon. Consequently, the tampon can be supplied to the packing station with the withdrawal cord being fixedly attached thereto. Since the withdrawal cord covers the end of the tampon, the user can easily detach the withdrawal cord from the tampon when opening the tampon package and before inserting it into the body cavity.

The diameter of the face of the push-rod is smaller than the first passage opening of the carrier jaws so that the push-rod may be accommodated therein while leaving an annular space therearound.

This ensures an unobjectionable feeding of the blank into the tampon press, the withdrawal cord, due to the friction between the withdrawal cord and the closed wall of the passage opening formed by the carrier jaws in the transmitting device for the blank, being longitudinally extending in a direction parallel to the central axis, there being sufficient space between the push-rod and the wall of the passage opening.

The carrier jaws comprise at least three jaws, each of the jaws being movably affixed to the basic body by being pivotable about jaw axes parallel to the central axis of the apparatus and disposed at equal radial distances from each other in a jaw axis circle. The jaw axis circle is concentric to the central axis. The jaws may then be moved by pivoting into the first and second positions. Still more specifically, the means for moving the jaws by pivoting into the first and second positions comprise levers. Each lever is of equal length and one end of each is pivotably coupled to the jaws adjacent the jaw axis. The other end of the lever is pivotably mounted to a coupling ring, which coupling ring is concentric to the central axis and has a diameter greater than the jaw axis circle. The coupling ring is adopted to oscillate thereby moving the jaws through the action of the levers into the first and second positions. This permits a simple yet effective arrangement of the carrier jaws under optimum dynamic conditions.

The carrier jaws are provided with curved, convex sides and the free ends of the carrier jaws have pointed edges. Each of the edges slidably engages the convex curved side of an adjacent carrier jaw so that when the jaws are moved into the first position, the convex curved side defines a portion of the wall of the first passage opening.

This provides that the walls of the passage opening formed by the carrier jaws will always be closed irrespective of the position of the pivoting carrier jaws at any point in time.

Each of the jaws have concavely curved ends ending in pointed edges. When the jaws are moved into the second position, a pointed edge of each jaw faces a pointed edge of an adjacent jaw with the curved ends of each jaw defining a fraction of the walls of the second passage opening. This ensures that the carrier jaws with their concave surface sections extending beyond the lines of contact with the tapered edges of the adjacent carrier jaws form a circular opening in the second position for receiving the tampon, the diameter of said opening being adjusted to the diameter of the tampon so that the latter retains its form in the radial direction when being subjected in the axial direction to at least an axial pressure sufficient for pressing the withdrawal cord onto the withdrawal end of the tampon.

DETAILED DESCRIPTION OF THE INVENTION

Figure 1:
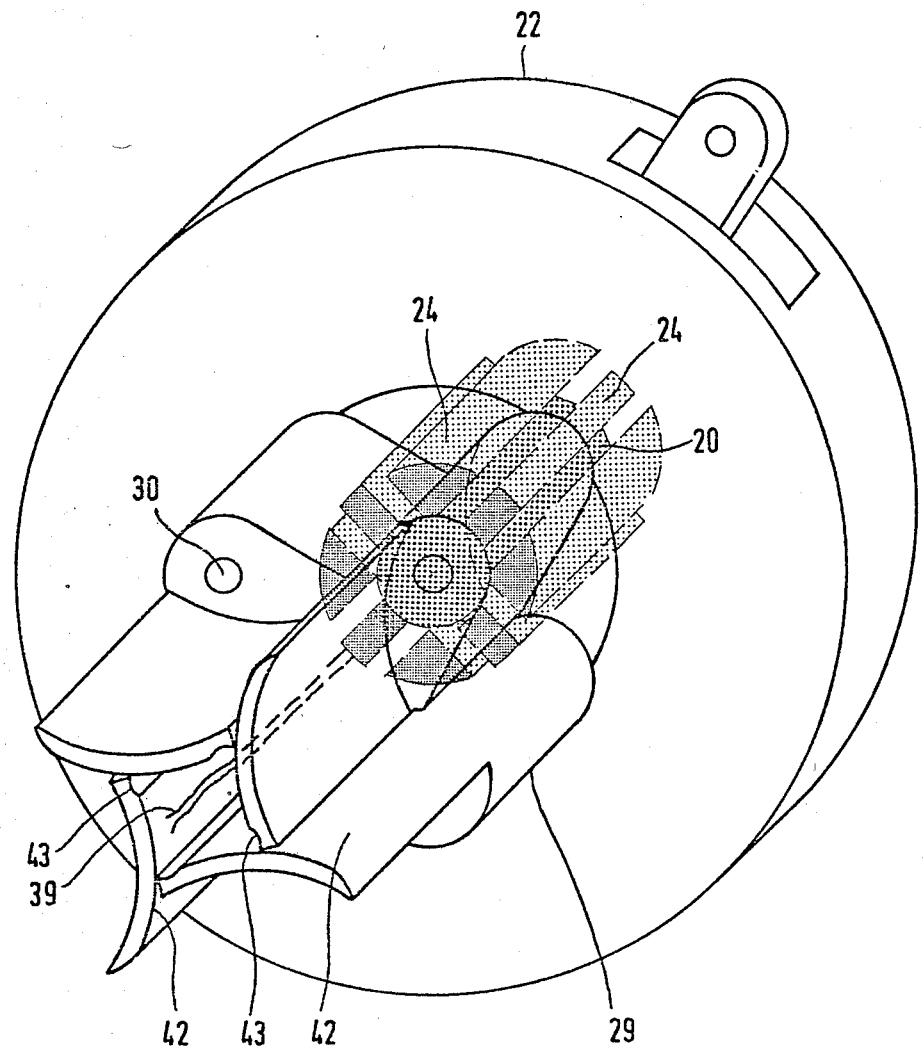
FIG. 1 shows an apparatus with a transmitting device arranged before a tampon press, in diagrammatic view.
Figure 3:
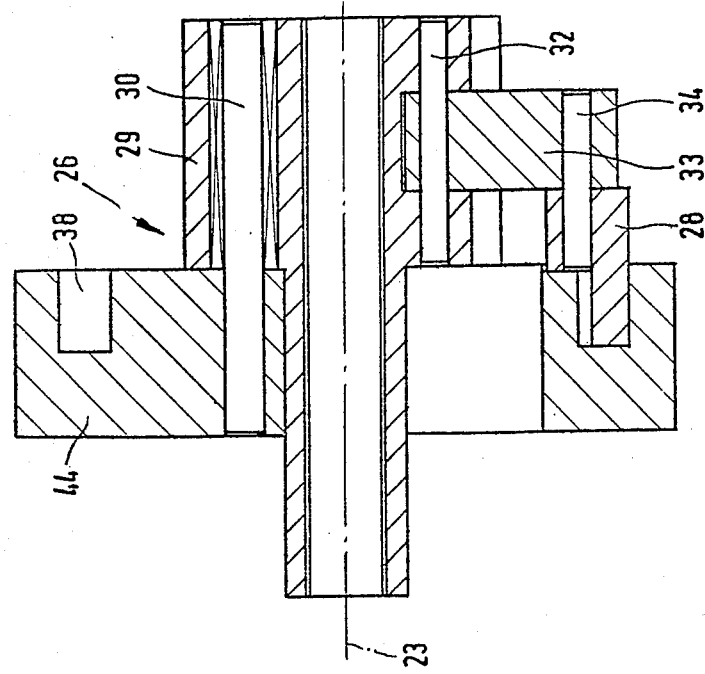
FIG. 3 is a section along line III—III in FIG. 2.

In the figures, there is illustrated an apparatus for transmitting a blank 20, consisting of absorbent material, particularly fiber material, for the manufacture of tampon 21, particularly for female hygiene, to a tampon press 22, the pressing jaws 24 of which are adapted for radial movement in a transverse plane to a central axis 23 of the apparatus and form a continuous press opening 25. A transmitting device 26 for the blank 20 is disposed before the tampon press, before said transmitting device there being arranged a push-rod 27 which is axially movable in the direction of the central axis 23 up to the press opening 25 (FIG. 7).

The transmitting device 26 consists of a basic body 44, in which a coupling ring 28 is pivotally mounted. Four carrier jaws 29 are disposed at parts of the basic body 44 lying within the coupling ring and are pivotable about pivots 30 lying at equal angular distances on a circle concentric to the central axis 23 or the coupling ring 28, respectively. The pivots consist of axes extending parallel to the central axis 23, i.e., the carrier jaws 29 are pivotable in a plane transverse to the central axis 23. In the area of the substantially inwardly directed ends of the carrier jaws 29, which are formed as tapered edges 31, said carrier jaws are articulated by bolts 32 on levers 33, the other end of which is pivotally connected through bearing bolts 34 to the coupling ring 28. The bearing bolts 34 are disposed on a common circle at equal circumferential distances, the center of the circle being the central axis 23. The levers 33 are of equal length in each case. The distances of the bolts 32 from the center of the pivots 30 of the associated carrier jaws are likewise equal. A connecting rod 35 is articulated by means of a bolt 36 to a bearing boss 37 of the coupling ring 28, which is supported by a circular groove 38 in the basic body 44 and adapted for reciprocating movement by a driving device not shown in the drawing, which engages at the connecting rod 35.

In the direction of the central axis 23, the carrier jaws 29 are of larger dimensions than the free length of a withdrawal cord 39 of the blank 20 so that the latter is completely received by the carrier jaws when the blank or the tampon respectively, are within the tampon press 22. Of course, the length of the carrier jaws could also only be adjusted to the length of the tampon, if blanks without a withdrawal cord are to be treated.

Figure 6:
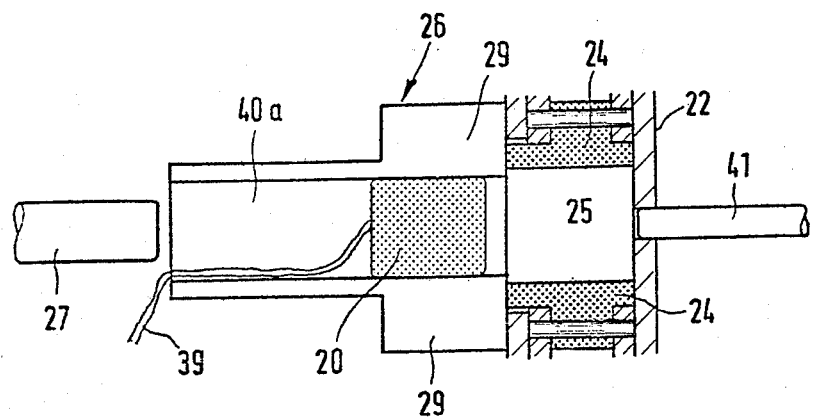
FIGS. 6–10 are longitudinal sections of the total apparatus, illustrating different working phases.
Figure 7:
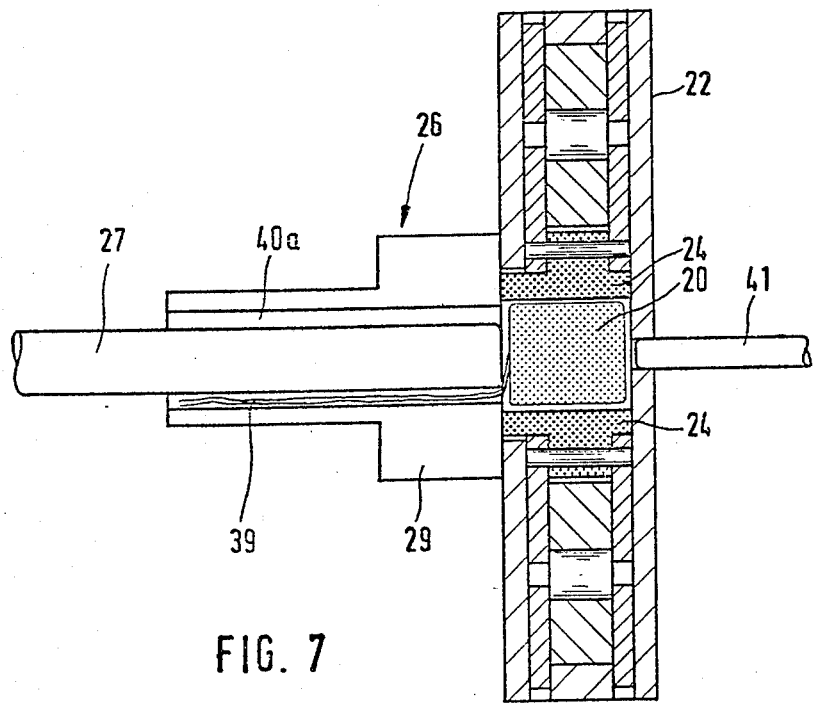

As apparent from FIGS. 6 and 7, the diameter of the face of the push-rod 27 is smaller than the passage opening 40a of the carrier jaws 29 in their first position for the blank 20. Consequently, as shown in FIG. 7, the blank can be accurately transferred by the push-rod into the tampon press 22, it being possible, due to sufficient space, to subsequently pull the withdrawal cord 39 without difficulty into the space between push-rod and wall of the passage opening 40a and to keep it there until the tampon is pushed out after the pressing step.

Figure 8:
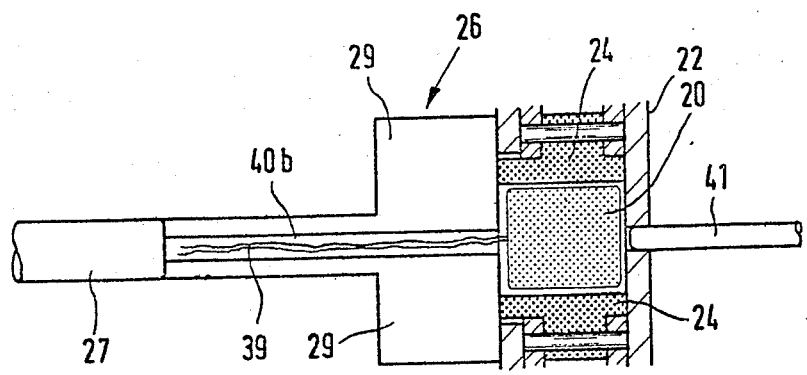
Figure 9:
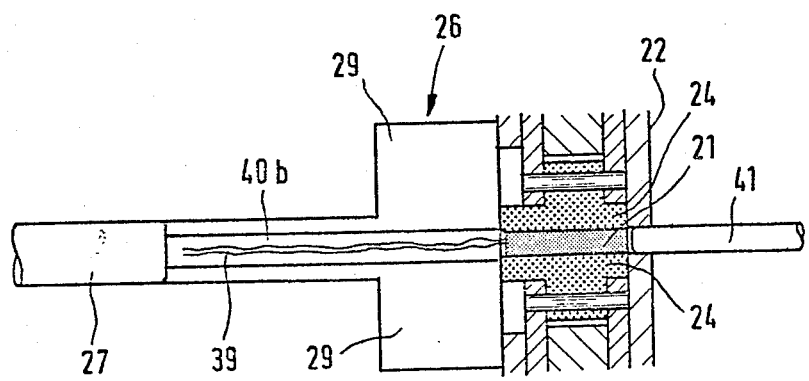
Figure 10:
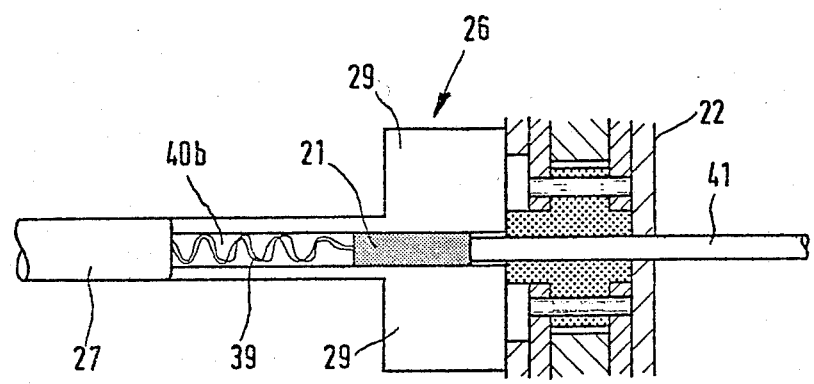

FIGS. 8 and 9 show that the face of the push-rod 27 is however dimensioned such that the passage opening 40b in the second position of the carrier jaws 29 for the receipt of the tampon 21 lies against the end of the carrier jaws facing away from the tampon press and closes the passage opening 40b.

An ejector mandrel 41 is disposed on the side of the tampon press 22 facing away from the transmitting device and adapted for reciprocating movement coaxially to the central axis 23 and serves for ejecting the tampon 21 from the tampon press 22 into the transmitting device 26 and against the push-rod 27, during which the withdrawal cord assumes substantially a spiral shape and is finally pressed onto the withdrawal end of the tampon in becoming hooked with the fibers thereof.

Figure 2:
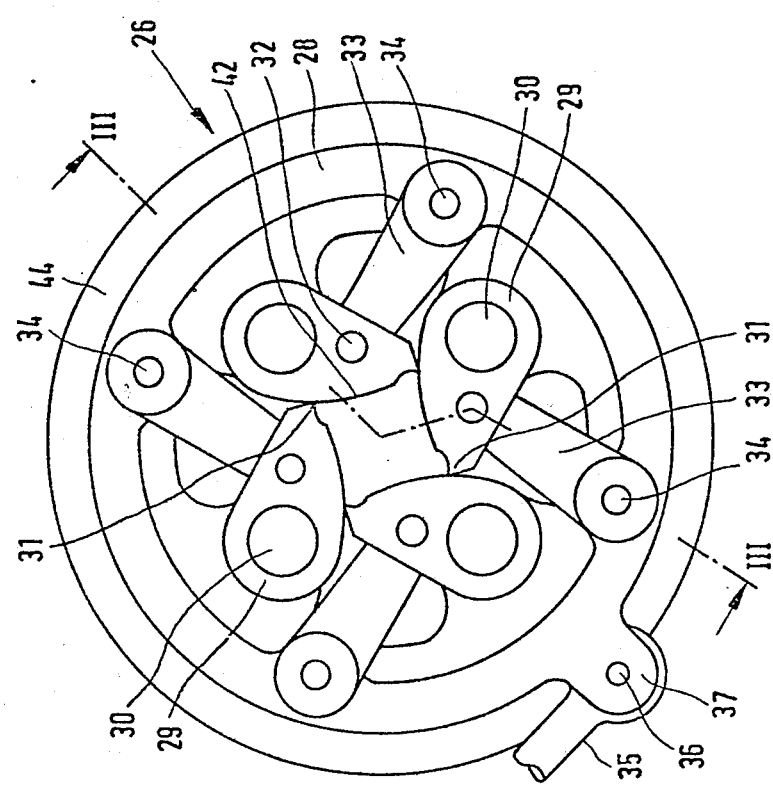
FIG. 2 is a view of the transmitting device with four carrier jaws in the first position for receiving a blank.
Figure 5:
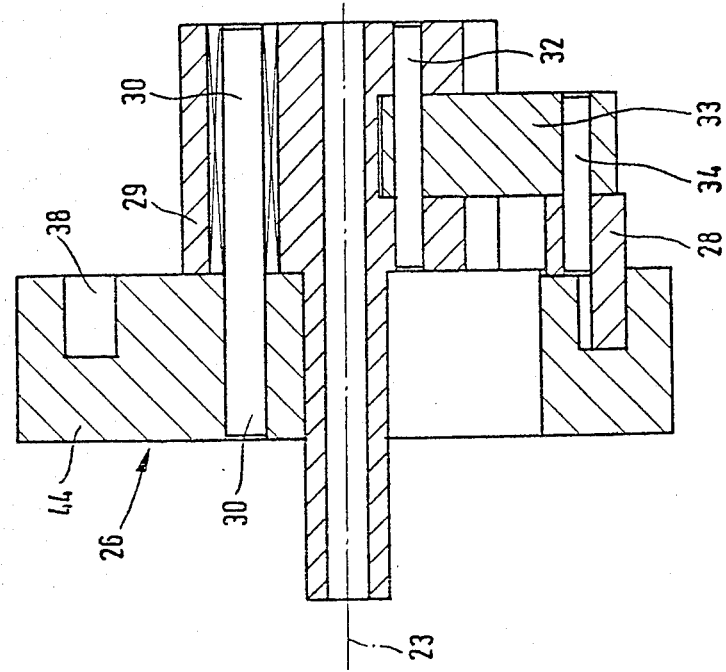
FIG. 5 is a section along line V—V in FIG. 4.
Figure 4:
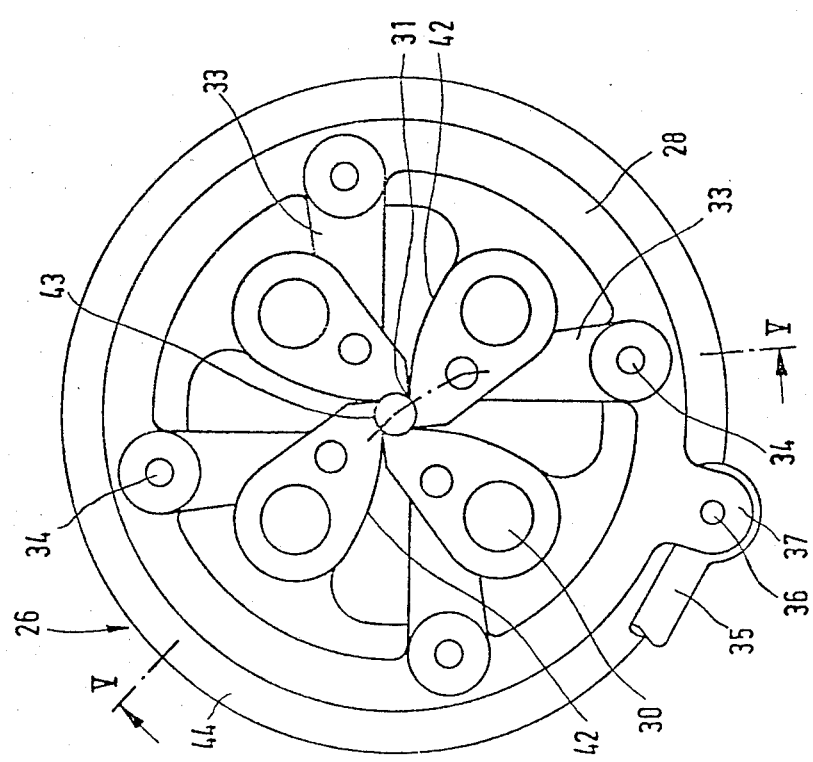
FIG. 4 shows the transmitting device according to FIG. 2 with the carrier jaws in the second position for receiving a tampon.

As FIGS. 2 and 4 show, the carrier jaws 29 form an always closed wall for the passage opening 40a; 40b, which is due to the fact that the tapered edges 31 slidingly engage the free ends of the carrier jaws 29 in each case at the side 42 of an adjacent carrier jaw 29 facing towards them and that the tapered edges during the synchronous pivoting movement of the carrier jaws describe an envelope circle corresponding to the convex curve shape of the side 42 of the adjacent carrier jaw. The tapered edges 31 of the carrier jaws 29 abut in their second position, adjusted to the cross-section of the tampon 21, against the end of the convex curve shape of the side 42 of the adjacent carrier jaw facing the tapered edges, said end being followed in each case by a concave surface 43 which extends up to the tapered edge 31 and the arc length of which is a fraction of the circumference of a circular cylinder with a diameter corresponding approximately to the tampon, said fraction corresponding to the number of the carrier jaws.

In operation, the blank 20 is pushed by the push-rod 27 through the polygonal passage opening 40a of the transmitting device 26 into the tampon press 22 (FIGS. 6, 7). After the push-rod has been moved out of the transmitting device 26, the latter interlocks the carrier jaws 29 to the circular cylindrical passage opening 40b by turning of the coupling ring 28, during which the withdrawal cord 39 is taken along by the carrier jaws 29 in the direction of the central axis 23.

In the following step, the blank 20 is pressed in the tampon press in the usual manner to form the tampon 21. Thereafter, the tampon 21 is pushed by the ejector mandrel 41 out of the tampon press 22 and into the circular cylindrical passage opening 40b of the transmitting device 26, associated with the second position of the carrier jaws 29, in the direction of the push-rod 27 which closes the passage opening 40b of the transmitting device. During this, the tampon 21 with its compressed mass pushes the withdrawal cord 39 ahead of it until the withdrawal cord is pressed against the tampon 21 by the reaction force of the push-rod 27.

It is thus apparent that the withdrawal cord lies against the tampon only at the withdrawal end thereof and can be brought into an extended position before the tampon is put to use, without there being the danger that fibers of the tampons become detached or loosened. Moreover, it will be understood that, instead of the described four carrier jaws, there can also be used three but also more than four carrier jaws for the transmitting device, if this should be desired.

I claim:

1. In an apparatus for compressing a blank comprising absorbent material into a compressed tampon, said apparatus having:

a transmission device for containing a blank upstream of a tampon press;

said tampon press having press jaws forming a continuous opening and press jaw means for opening said jaws to receive said blank and for closing said jaws to compress said blank;

a push rod and means for reciprocating said push rod to transmit said blank from said transmission device into said press; and an ejector mandrel and means for reciprocating said ejector mandrel for ejecting said compressed tampon from said press;

the improvement wherein:

said transmission device comprises a stationary basic body having an axis aligned with the central axis of the apparatus and a plurality of carrier jaws movably fixed to said basic body;

said carrier jaws being movable with respect to each other so as to form, in a first position, a first passage opening having closed walls defined by said jaws for enclosing said blank;

said jaws being movable with respect to each other so as to form, in a second position, a second passage opening having closed walls defined by said jaws for enclosing said compressed tampon;

said first and second passage openings being coaxial with the central axis of said apparatus;

said carrier jaws having a length in the direction of the central axis, at least equal to the length of the blank;

said push rod being axially positioned upstream of said transmission device and adapted to reciprocate into and out of said first passage opening for transmitting said blank into said press;

said ejector mandrel being axially positioned downstream of said press and having a diameter smaller than that of said compressed tampon and adapted to reciprocate into and out of said press;

carrier jaw moving means for moving said carrier jaws into said first and second positions;

said apparatus adapted for operation in sequence wherein said carrier jaws are moved into said first position by said carrier jaw moving means and said press jaws are opened by said press jaw means;

said push rod is reciprocated into said first passage opening to transfer said tampon blank into said opened press jaws;

said press jaws are closed by said press jaw means to compress said blank, said carrier jaws are moved into said second position by said carrier jaw moving means, and said push rod is reciprocated to close the upstream end of said second passage opening; and said ejector mandrel is reciprocated into said closed press jaws to eject said compressed tampon into said second passage opening.

2. The apparatus of claim 1 for transmitting tampon blanks provided with a withdrawal cord to said tampon press, wherein the length of the carrier jaws in the direction of the central axis is greater than the free length of the withdrawal cord of the tampon blank.

3. The apparatus of claim 1 wherein the leading face of the push rod is small enough to be accommodated within the first passage opening of the carrier jaws while leaving an annular space therearound.

4. The apparatus of claim 1 wherein:
said carrier jaws comprise at least three jaws;
each of said jaws being movably affixed to said basic body by being pivotable about jaw axes parallel to the central axis of the apparatus and disposed at equal radial distances from each other in a circle concentric to the central axis;
whereby said jaws may be moved, by pivoting, into said first and second positions.

5. The apparatus of claim 4 wherein the means for moving said jaws, by pivoting into said first and second positions, comprises:
levers, each of equal length, one end of each permanently coupled to said jaws at said jaw axis and the other end, permanently mounted to a coupling ring, said coupling ring being concentric to said central axis and having a diameter greater than the jaw axes circle, said coupling ring being adjusted to rotate thereby moving said jaws, through the use of said levers into said first and second positions.

6. The apparatus of claim 1 wherein the carrier jaws have curved convex sides and the free ends of the carrier jaws have pointed edges, each of which edges slidingly engage the convex curved side of an adjacent carrier jaw, whereby when said jaws are moved into said first position, said convex curved side defines a portion of the wall of said first passage opening.

7. The apparatus in accordance with claim 1 wherein each of the jaws have concavely curved ends ending in pointed edges and when said jaws are moved into said second position, a pointed edge of each jaw forms a pointed edge of an adjacent jaw with the curved ends of each jaw defining a fraction of the walls of said second passage opening.

* * * * *